US008323722B2

(12) United States Patent
Rabiei

(10) Patent No.: US 8,323,722 B2
(45) Date of Patent: Dec. 4, 2012

(54) PROCESSING OF BIOCOMPATIBLE COATING ON POLYMERIC IMPLANTS

(75) Inventor: Afsaneh Rabiei, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 720 days.

(21) Appl. No.: 12/505,101

(22) Filed: Jul. 17, 2009

(65) Prior Publication Data
US 2010/0016985 A1 Jan. 21, 2010

Related U.S. Application Data

(60) Provisional application No. 61/082,003, filed on Jul. 18, 2008.

(51) Int. Cl.
B05D 3/02 (2006.01)
B05D 3/06 (2006.01)
A61L 27/32 (2006.01)
A61F 2/28 (2006.01)

(52) U.S. Cl. ...... 427/2.1; 427/2.24; 427/2.25; 427/2.26; 427/2.27; 427/2.29; 427/372.2; 424/423; 623/23.56; 623/23.57

(58) Field of Classification Search .................... 427/2.1, 427/2.24, 2.26, 2.27, 372.2
See application file for complete search history.

(56) References Cited

U.S. PATENT DOCUMENTS

| 6,208,881 | B1 * | 3/2001 | Champeau | ..................... | 600/374 |
| 6,296,667 | B1 * | 10/2001 | Johnson et al. | ............ | 623/23.61 |
| 6,730,324 | B2 | 5/2004 | Troczynski et al. | | |
| 2004/0022825 | A1 * | 2/2004 | Lagow | ........................... | 424/423 |
| 2006/0210494 | A1 * | 9/2006 | Rabiei et al. | ..................... | 424/57 |

FOREIGN PATENT DOCUMENTS

| WO | WO 94/22513 | 10/1994 |
| WO | WO 2005/067993 | 7/2005 |

OTHER PUBLICATIONS

Hontsu et al. Pulsed Laser Deposition of Bioceramic hydroxyapatite thin films on polymer materials. Jpn. J. Appl. Phys. vol. 35 (1996) pp. 1208-1210. Sep. 1996.*
Feng et al. Highly adhesive calcium phosphate layer on UHMWPE prepared by IBAD. Current applied physics vol. 1 pp. 213-217 (2001).*
Miao et al. Porous calcium phosphate ceramics prepared by coating polyurethane foams with calcium phosphate. Materials Letters, 58 [3-4] (2004), pp. 397-402.*
Ha et al. Surface activation of polyether ether ketone (PEEK) and formation of calcium phosphate coatings by precipitation. Journal of Materials Science: Materials in Medicine vol. 8 (1997) 683-690.*
Bloebaum, R.D., et al., "Retrieval Analysis of a Hydroxyapatite-Coated Hip Prosthesis," Clin. Orthop. Rel. Res., 1991, pp. 97-102, vol. 267.
Cao, Y., et al., "Water Vapour-Treated Hydroxyapatite Coatings after Plasma Spraying and Their Characteristics," Biomaterials, 1996, pp. 419-424, vol. 17(4).
Chou, L., et al., "Effects of Hydroxylapatite Coating Crystallinity on Biosolubility, Cell Attachment Efficiency and Proliferation In Vitro," Biomaterials, 1999, pp. 977-985, vol. 20.
Cook et al., "The Effect of Surface Macrotexture on the Mechanical and Histologic Characteristics of Hydroxylapatite-Coated Dental Implants," J Oral Implant, 1993, pp. 288-294, vol. 19(4).
Cooley et al., "The Advantages of Coated Titanium Implants Prepared by Radiofrequency Sputtering from Hydroxyapatite," J Prosthet. Dent., 1992, pp. 93-100, vol. 67.
Dalton et al., "In Vivo Mechanical and Histological Characteristics of HA-Coated Implants Vary with Coating Vendor," J Biomed Mater Res., 1995, pp. 239-245, vol. 29.
De Bruijn et al., "Influence of Crystal Structure on the Establishment of the Bone-Calcium Phosphate Interface In Vitro," Cells and Mater, 1993, pp. 407-417, vol. 3(4).
Ding et al., "Characterization of Hydroxyapatite and Titanium Coatings Sputtered on Ti-6A1-4V Substrate," J. Biomedical Mater. Res., 1999, pp. 266-279, vol. 44.
Feddes, B., et al., "Bulk Composition of R.F. Magnetron Sputter Deposited Calcium Phosphate Coatings on Different Substrates (Polyethylene, Polytetrafluoroethylene, Silicon)," Surf. Coat. Technol., 2004, pp. 346-355, vol. 185.
Filiaggi et al., "Characterization of the Interface in the Plasma-Sprayed HA Coating/Ti-6A1-4V Implant System," J. Biomed. Mater. Res., 1991, pp. 1211-1229, vol. 25.
Gabbi et al., "Physical, Chemical and Biological Characterisation of Hydroxyapatite Coatings of Differentiated Crystallinity," Fourth World Biomaterials Congress, Berlin, Germany, Apr. 24-28, 1992, p. 5.
Guise et al., "Interleukin-1 Receptor Antagonist Inhibits the Hypercalcemia Mediated by Interleukin-1," J. Bone Miner. Res., 1993, pp. 583-587, vol. 8(5).
Ha et al., "Plasma-Sprayed Hydroxylapatite Coating on Carbon Fibre Reinforced Thermoplastic Composite Materials," Journal of Materials Science: Materials in Medicine, 1994, pp. 481-484, vol. 5.
Hench et al., "Ceramics, Glasses, and Glass-Ceramics," Biomaterials Science: An Introduction to Materials in Medicine, 1996, p. 73-84, Academic Press, San Diego.
Hoppe et al., "Osteoblast Response to HA Ceramics of Different Crystallinity," J. Dent. Res., 1996, p. 78, vol. 75, Abstract No. 482.
Kaufman et al., "Target Processes," Operation of Broad-Beam Sources, 1987, pp. 107-117, Commonwealth Scientific Corporation, Alexandria, VA.
Kay, "Calcium Phosphate Coatings for Dental Implants—Current Status and Future Potential," Dent. Clin. North Amer., 1992, pp. 1-18, vol. 36(1).
Kumar et al., "Modulus and Hardness Evaluations of Sintered Bioceramic Powders and Functionally Graded Bioactive Composites by Nano-Indentation Technique," Materials Science and Engineering, 2002, pp. 230-236, vol. A338.

(Continued)

Primary Examiner — Timothy Meeks
Assistant Examiner — Cachet Sellman
(74) Attorney, Agent, or Firm — Womble Carlyle Sandridge & Rice, LLP

(57) ABSTRACT

The present invention provides polymeric substrates comprising a biocompatible coating and methods of preparation thereof. In particular, the coating may be a ceramic material, especially a calcium phosphate material, which may be functionally graded. The invention provides the ability to apply high quality coatings to polymeric substrates without damaging the substrate (e.g., melting the polymeric material). The functionally graded coating can provide crystalline calcium phosphate near the coating interface with the substrate and provide amorphous calcium phosphate at the outer surface of the coating.

13 Claims, No Drawings

OTHER PUBLICATIONS

Lacefield, "Characterization of Hydroxylapatite Coatings," *J Oral Implant*, 1994, pp. 214-220, vol. 20(3).

Lacefield et al., "Hydroxyapatite Coatings," *Bioceramics: Material Characteristics Versus In Vivo Behavior*, 1988, pp. 72-80, Annals of the New York Academy of Science, New York.

Legeros, "Calcium Phosphate Materials in Restorative Dentistry: A Review," *Adv in Dent Mater*, 1988, pp. 164-180, vol. 2(1).

Legeros, "Calcium Phosphate Biomaterials in Preventive and Restorative Dentistry," *Monographs in Oral Science*, 1991, pp. 154-192, Karger, Basel, Switzerland.

Lemons, "Hydroxyapatite Coatings," *Clin. Orthop.*, 1988, pp. 220-223, vol. 235.

Lewis, "Hydroxyapatite-Coated Bioalloy Surfaces: Current Status and Future Challenges," *Biomed. Mater. Eng.*, 2000, pp. 157-188, vol. 10.

Lucas et al., "Calcium Phosphate Coatings for Medical and Dental Implants," *Colloids and Surfaces A: Physiochemical and Engineering Aspects*, 1993, pp. 141-147, vol. 77.

Luo et al., "Low-Temperature Crystallization of Calcium Phosphate Coatings Synthesized by Ion-Beam-Assisted Deposition," *J. Biomed. Mater. Res.*, 1996, pp. 80-86, vol. 46.

Martin, "Biomaterials," *Introduction to Bioengineering*, 1996, pp. 339-360, Oxford University Press, Oxford, UK.

Nery et al., "Tissue Response to Biphasic Calcium Phosphate Ceramic with Different Ratios of HA/βTCP in Periodontal Osseous Defects," *J. Periodontal*, 1992, pp. 729-735, vol. 63(9).

Ozeki et al., "Phase Composition of Sputtered Films from a Hydroxyapatite Target," *Surf. Coat. Technol.*, 2002, pp. 54-61, vol. 160.

Passi-Even et al., "Ontogenesis of Ultrastructural Features During Osteogenic Differentiation in Diffusion Chamber Cultures of Marrow Cells," *J. Bone Miner. Res.*, 1993, pp. 589-595, vol. 8(5).

Rabiei et al., "Processing and Development of Nano-Scale HA Coatings for Biomedical Application," *Journal of Mater. Sci. and Eng.*, vol. C, in review.

Radin et al., "Plasma Spraying Induced Changes of Calcium Phosphate Ceramic Characteristics and the Effect on In Vitro Stability," *J. Mater. Sci. Mater. Med.*, 1992, pp. 33-42, vol. 3.

Rivero et al., "Calcium Phosphate-Coated Porous Titanium Implants for Enhanced Skeletal Fixation," *J. Biomed. Mater. Res.*, 1988, pp. 191-201, vol. 22.

Schneider et al., "Implant Surface Roughness Affects Osteoblast Gene Expression," *J. Dent. Res.*, 2003, pp. 372-376, vol. 82(5).

Silva et al., "Adhesion and Microstructural Characterization of Plasma-Sprayed Hydroxyapatite/Glass Ceramic Coatings onto Ti-6A1-4V Substrates," *Surf. Coat. Technol.*, 1998, pp. 191-196, vol. 102.

Søballe, K., et al., "Hydroxyapatite Coating Converts Fibrous Tissue to Bone around Loaded Implants," *J Bone Joint Surg*, 1993, pp. 270-277, vol. 75-B(2).

Thomas et al., "An Evaluation of Variables Influencing Implant Fixation by Direct Bone Apposition," *J. Biomed. Mater. Res.*, 1985, pp. 875-901, vol. 19.

Van Dijk et al., "Influence of Annealing Temperature on RF Magnetron Sputtered Calcium Phosphate Coatings," *Biomaterials*, 1996, pp. 405-410, vol. 17(4).

Yan et al., "Characterization of Chemical Inhomogeneity in Plasma-Sprayed Hydroxyapatite Coatings," *Biomaterials*, 2003, pp. 2585-2592, vol. 24.

Yang et al., "A Review on Calcium Phosphate Coatings Produced Using a Sputtering Process—An Alternative to Plasma Spraying," *Biomaterials*, 2005, pp. 327-337, vol. 26.

Zablotsky, "The Surgical Management of Osseous Defects Associated with Endosteal Hydroxyapatite-Coated and Titanium Dental Implants," *Dent. Clin. North. Amer.*, 1992, pp. 117-149, vol. 36(1).

* cited by examiner

PROCESSING OF BIOCOMPATIBLE COATING ON POLYMERIC IMPLANTS

CROSS-REFERENCE TO RELATED APPLICATIONS

This application claims the benefit of U.S. Provisional Application No. 61/082,003, filed Jul. 18, 2008, which is incorporated by reference herein in its entirety.

FIELD OF THE INVENTION

The present invention relates to biocompatible coatings. In particular, the invention is related to polymeric implants coated with a biocompatible calcium phosphate coating and methods of preparation of such coated polymeric implants.

BACKGROUND OF THE INVENTION

Various types of implants are commonly used in biomedical applications, particularly in the dental and orthopedic fields. Often, implants are associated with use in areas of hard tissue (i.e., cartilage, bone, etc.), and the implants generally comprise hard, durable materials, such as metals, particularly titanium. Increasingly, polymeric materials, such as polyetheretherketone (PEEK) and polyurethane (PU), are being likewise used in medical application, including medical implants.

Medical implants are commonly plagued by poor biointegration into the surrounding tissue. Often, the body responds to the implant as to any foreign object by isolating the implant with a flexible layer of fibrous tissue that can easily cause an implant to loosen. This is detrimental to the usefulness of the implant. For example, in the case of dental implants, loosening of the implant can result in loss of the implanted tooth and can also lead to infections around the loosened implant.

It is commonly known in the art to apply various coatings to orthopedic components and other medical devices for a variety of reasons, including facilitating implant fixation and bone in-growth. See, *Handbook of Materials for Medical Devices*, Davis, J. R. (Ed.), Chapter 9, "Coatings", (2003). In particular, calcium phosphate phases are useful as coatings for facilitating bone in-growth. One calcium phosphate phase, hydroxyapatite (HA) [$Ca_{10}(PO_4)_6(OH)_2$], is the primary mineral content of bone and calcified cartilage, representing 43% by weight of bone. Because of the chemical and crystallographic similarities with the inorganic components of bone, applying a thin layer of HA, or other calcium phosphate layer, to the surface of a metal implant, such as a titanium implant, can promote osseointegration and increase the mechanical stability of the implant. In fact, many studies have demonstrated that dental and orthopedic implants coated with plasma sprayed HA promote greater direct bone attachment and higher interfacial strength compared to the uncoated titanium implants. Numerous problems with the HA coatings, however, have also been cited, including variation in bond strength at the coating-metal interface, variation in structural and chemical properties, and non-uniformity in coating density.

Hydroxyapatite coatings are generally comprised of varying percentages of crystalline HA, tricalcium phosphate, and amorphous calcium phosphate. The ratio of HA to tricalcium phosphate has been reported to be crucial for bone regeneration. It has also been reported that the dissolution rate of a HA coating is correlated to the biochemical calcium phosphate phase of the coating. It is known that coatings with more crystalline HA are more resistant to dissolution. Conversely, coatings with increased concentrations of amorphous calcium phosphate and tricalcium phosphate are thought to predispose the HA coatings to dissolution. Since it has been suggested that the dissolution of calcium phosphate from the surface of the implant in the body is responsible for the bioactivity of the HA coating, knowledge of the crystalline content of the surface coating is critical to implant success. Some studies have indicated that bone responds differently to HA coatings of different crystallinity. These studies have indicated higher bone activity with well characterized HA coatings of higher crystallinity, while other studies suggest that some amorphous phase in the coatings is desirable and promotes a more stable interface with the biological environment. Still further studies have identified various structural factors that also affect the biological response of bone to HA coatings, including surface texture, porosity, and the presence of trace elements. Accordingly, it is beneficial for the characteristics of the implant surface to be precisely controlled during the implant process, particularly with respect to the crystalline content of the coating surface.

Because of its simplicity and versatility, plasma spraying is the most widely used technique for applying HA coatings onto implants. Although plasma spraying is fast and cost effective, the coatings have several flaws that could lead to implant failures. Plasma sprayed films exhibit a high porosity and only attach to the substrate surface through mechanical bonding (i.e., no intermolecular bonding). This leads to inconsistent bonding strengths. Plasma sprayed coatings are also relatively thick. Generally, coatings on commercially available plasma sprayed implants have a thickness of between 79 µm and 111 µm. Such thick coatings can lead to low fracture resistance. This, along with reduced bond strength, can lead to delamination, and detached fragments have very adverse effects on the implant, as well as the tissue surrounding it.

Providing HA coatings on polymeric substrates as opposed to metallic substrates amplifies the difficulty of obtaining a useful, quality implant. Despite the above flaws, plasma spraying is the only technique that has been briefly exercised for depositing HA coatings on polymeric implants, such as polyetheretherketone (PEEK) or carbon fiber reinforced PEEK (CF/PEEK) to improve their biocompatibility (see S. W. Ha, et al. (1994), *Journal of Materials Science: Materials in Medicine*, 5(6-7): 481-484). The pull-off test was used to measured the tensile adhesion strength of these coated substrates and was found to be only 2.8 MPa. Such low bonding strength is believed to have resulted from the evaporation of the CF/PEEK surface by the layer of HA particles reaching the PEEK surface at a temperature of about 1,650° C. Accordingly, there remains a need in the art for alternative technologies to provide biocompatible coatings on polymeric substrates, particularly implants.

SUMMARY OF THE INVENTION

The present invention is directed to polymeric substrates comprising ceramic coatings and methods of preparing such ceramic coated polymeric substrates. Any ceramic material may be used as a coating according to the invention and may be applied to any substrate having a surface that is at least partially comprised of a polymeric material, particularly a polymeric material that would be subject to at least partial damage (e.g., melting) at temperatures associated with coating techniques, such as plasma spray coating.

In certain embodiments, the present invention provides calcium phosphate (e.g., hydroxyapatite) coatings on polymeric substrates and methods of preparing such coated substrates. Particularly, the calcium phosphate coatings may be functionally graded. The coatings have can have a nanoscale grain structure to mimic the structure of bone itself and may be processed using Ion Beam Assisted Deposition to provide a stronger adhesion bonding between the coating the substrate. The coating can be doped with certain components, such as antimicrobial components, and have a tailored rate of release in the body.

Extensive in vivo research indicates that hydroxyapatite coated implants are more biocompatible and perform better than non-coated implants. The superior performance of HA coated implants is attributed to their more rapid osteointegration and the development of increased interfacial strength that results from the early skeletal attachment and increased bone contact with the implant surface.

The present invention allows for the addition of a calcium phosphate coating to a polymeric substrate without damaging the properties of the polymer. The invention also provides an improved lifetime for a coated implant by improving bond strength between the coating and the substrate, as well as facilitating the rapid integration into the surrounding body tissue for implants. This reduces the risk of implant rejection and the need for frequently replacing the implants.

In one aspect, the present invention is directed to a method for preparing a biocompatible coated substrate. In some embodiments, the method comprises providing a substrate having a surface including a polymeric material, and applying a calcium phosphate coating to the substrate. Preferably, the coating is applied at a temperature below the melting point of the polymeric material. In specific embodiments, the coating is applied using Ion Beam Assisted Deposition (IBAD). Particularly, the coating can be applied at ambient conditions.

The method of the invention can be carried out on substrates comprising a variety of polymeric materials. Non-limiting examples of polymeric materials that may be used include polyetheretherketone (PEEK), carbon fiber reinforced PEEK, and polyurethanes.

In certain embodiments, it may be useful to provide a protective coating to the polymeric substrate prior to coating with the calcium phosphate. Such coating may particularly be described as a thermal barrier coating in light of its ability to protect the polymeric substrate from high temperatures that may be applied at later stages of the method in certain embodiments. Preferably, any thermal barrier coating is applied to the substrate at a temperature below the melting point of the polymeric material and may be applied using IBAD. In specific embodiments, the thermal barrier coating comprises a metal or a metal oxide. Non-limiting examples of useful metal oxides include zirconia, yttrium stabilized zirconia, or combinations thereof.

In specific embodiments, it is possible according to the invention to form a coated substrate wherein the calcium phosphate is functionally graded. The application of the calcium phosphate through IBAD provides the coating material in an amorphous state. Accordingly, in some embodiments, it is useful to convert the amorphous calcium phosphate to crystalline calcium phosphate. Specifically, this may be done by heat-treating the calcium phosphate coating. In one embodiment, the heat-treating step comprises a microwave treatment. In another embodiment, the heat-treating step comprises a laser treatment.

After the calcium phosphate coating has been transformed to a crystalline state, it can be useful to form a second calcium phosphate coating over the first calcium phosphate coating. In certain embodiments, such method step particularly comprises applying a second calcium phosphate coating to the heat-treated first calcium phosphate coating at a temperature below the melting point of the polymeric material. The final coating applied by IBAD will be in the amorphous state, and the underlying, heat-treated calcium phosphate coating will be in a crystalline state, thus providing a functionally graded calcium phosphate coating. Such overall calcium phosphate is beneficially uniform in thickness and of a relatively thin dimension. In certain embodiments, the overall calcium phosphate coating has a thickness of about 100 nm to about 10 µm or about 500 nm to about 5 µm.

In one specific embodiment, the invention provides a method for preparing a polymeric substrate coated with a functionally graded calcium phosphate coating. The method comprises the following steps: providing a substrate having a surface comprising a polymeric material; applying a thermal barrier coating to the substrate using IBAD at ambient conditions; applying an amorphous calcium phosphate coating over the thermal barrier coating using IBAD at ambient conditions; heat-treating the amorphous calcium phosphate coating to crystallize the calcium phosphate coating, said heat-treating comprising a method selected from the group consisting of a microwave treatment, a laser treatment, and combinations thereof; and applying a second amorphous calcium phosphate coating to the heat-treated first calcium phosphate coating using IBAD at ambient conditions.

In another aspect, the present invention also provides a biocompatible coated substrate. In certain embodiments, the coated substrate comprises a substrate having a surface formed of a polymeric material and a biocompatible coating layer comprising calcium phosphate overlying at least a portion of the substrate surface and bonded thereto. Preferably, the calcium phosphate in the coating layer is in a crystalline form in an area of the coating layer proximal to the substrate and is in an amorphous form in an area of the coating layer distal to the substrate.

In some embodiments, the coated substrate may further comprise a thermal barrier coating between the substrate and the calcium phosphate coating layer. In specific embodiments, the thermal barrier coating comprises a material selected from the group consisting of zirconia, yttrium stabilized zirconia, or combinations thereof.

A variety of coated substrates may be formed according to the present invention. In one embodiment, the coated substrate is a prosthetic implant. In specific embodiments, the prosthetic implant is selected from the group consisting of a dental implant and an orthopedic implant.

Further, multiple type of calcium phosphate could be used in the coating according to the invention. In certain embodiments, the calcium phosphate is selected from the group consisting of hydroxyapatite, tricalcium phosphate, and mixtures thereof.

DETAILED DESCRIPTION

The present inventions now will be described more fully hereinafter. These inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Polymeric materials are increasingly being relied upon in medical applications as long-term, implantable devices. Polymeric materials may be used as dental or orthopedic implants, as well as other medical devices, such as artificial hearts, catheter tubing, feeding tubes, surgical drains, intraaortic balloon pumps, dialysis devices, protective gloves, medical garments, hospital bedding, wound dressings, and many further applications. As with metal substrates, however, to improve biointegration of medical implants formed of polymeric materials, it is useful to provide the substrate with some type of coating. For example, to improve osteointegration, it can be useful to provide the substrate with a coating comprising a material that can be described as a bone-substitute, bone-replacement, or bone-like material. One such type of materials is calcium phosphate containing materials (e.g., hydroxyapatite).

The substrate according to the invention can include any item or device wherein the presence of a ceramic coating, particularly a biocompatible coating, and preferably a coating providing increased osteointegration, would be advantageous. The substrate can particularly be an item or device implantable in an area where interaction or integration with bony formations is desired or expected. In one embodiment of the invention, the substrate includes a prosthetic implant. According to another embodiment, the substrate includes a dental implant. In yet another embodiment of the invention, the substrate includes an orthopedic implant. Items useful as substrates for coating according to the invention include, but are not limited to the following: dental screws, cylinders, blades, plates, and posts; partial or total joint replacements, including hip, knee, shoulder, and ankle replacements; orthopedic screws, pins, plates, bolts, nuts, rods, nails, and wires; and other similar dentally or orthopedically implantable substrates.

The coated substrate of the invention is particularly useful in the dental orthopedic fields. Accordingly, in one embodiment of the invention, the substrate comprises a dental implant. In another embodiment, the substrate comprises an orthopedic implant.

Coated substrates according to the invention are also useful generally in the area of bone reconstruction. For example, the coated substrate could be used in a partial or total joint replacement, in replacement of an area of missing bone, and as a piece for treating bone fracture, such as a screw or plate.

As previously noted, typical coating methods, such as plasma spraying, are carried out at high temperatures, typically above the melting point of many polymeric materials that would be desirable as a medical device, such as an implant. The present invention overcomes this problem by providing a method of coating a substrate formed of a polymeric material and coated substrates prepared according to the method.

Any polymeric material useful in forming a medical device may be used according to the present invention. Non-limiting examples of polymeric materials that may be used according to the invention include acrylates, methacrylates, polyglycolic-polylactic acid copolymers, polyhydroxybutyrates, polyesters (such as DACRON®), expanded polytetrafluoroethylene (ePTFE), ethylene vinyl acetate copolymers, and combinations thereof.

In a specific embodiment, a polymeric material that may be used as a substrate according to the invention is polyetheretherketone (PEEK), which is a high molecular weight, semicrystalline, thermoplastic material having high chemical and thermal stability, high mechanical strength, stiffness, toughness, and fatigue capabilities. The modulus of elasticity of PEEK (around 4 to 40 GPa) roughly matches that of natural bone (e.g., around 30 GPa), and this makes PEEK particularly useful for various biomedical implant applications to avoid the necessity of stress shielding issues often faced with metallic implants. For example, titanium and titanium alloys are orders of magnitude higher in stiffness than natural bone, and dental implants formed from such materials absorb most of the forces of mastication, thus effectively shielding the surrounding bone from such stresses. Polyetheretherketone has high chemical and thermal stability and does not experience any degradation of chemical or mechanical properties when exposed in simulated body fluid. Polyetheretherketone can also be sterilized using gamma radiation or ethylene oxide without any hydrolytic decomposition. Further, PEEK is transparent in some diagnostic techniques (e.g., X-ray, CT, and MRI), which is an important factor for monitoring the healing process around implants. In addition to plain PEEK, modified PEEK, such as carbon fiber reinforced PEEK (CF/PEEK) may also be used according to the invention. Polyetheretherketone is a particularly favored material for use in spinal implants.

In another embodiment, a polymeric material that may be used as a substrate according to the invention is polyurethanes. Although they can take on many forms, polyurethanes can be formulated to provide good biocompatibility, flexural endurance, high strength, high abrasion resistance, and processing versatility over a wide range of applications. Polyurethanes can outperform many other materials in flexibility, tear resistance, and abrasion resistance. Of course, the preceding is not meant to overly limit the scope of the invention. Rather, PEEK and polyurethanes are merely representative examples of polymeric materials that could be used according to the invention, and any polymeric material that may be used in a medical device that would benefit from being coated with an osteointegration enhancing material (e.g., calcium phosphate), or a ceramic material generally, could be used as a substrate according to the present invention.

In one aspect, the present invention provides a method for providing a biocompatible coated substrate by applying a ceramic coating on the substrate. Preferably, the method comprises applying a biointegration-improving coating on the substrate. Particularly, the substrate comprises a polymeric material. More particularly, the substrate can be defined as comprising a surface (e.g., and external surface), and the surface at least partially comprises the polymeric material. In some embodiments, the substrate may be completely substantially formed of the polymeric material. In other embodiments, the substrate may be formed of a different material (e.g., metal, glass, or the like), and the substrate may have an external coating or layer formed of the polymeric material.

In some embodiments, the method comprises providing a substrate having a surface comprising a polymeric material, and applying a calcium phosphate coating to the substrate. In some embodiments it may be useful to process the surface prior to applying the calcium phosphate coating. Examples of processing that may be useful include grinding and/or polishing of the surface.

Preferably, the calcium phosphate coating is applied at a temperature below the melting point of the polymeric material. It has been discovered according to the invention that forming a viable coating on a polymeric substrate requires due care to avoid disrupting the integrity of the polymeric substrate surface. For example, plasma spraying was used in a test carried out in Switzerland to apply hydroxyapatite to a PEEK or CF/PEEK implant. Although the coating was successfully applied, the coating exhibited a very poor adhesion strength of only 2.8 MPa, which would insufficient to survive in vivo in long term implantation. Although not wishing to be bound by theory, it is believed that the poor adhesion strength resulted from the high temperature of the HA plasma spray deposition process, which could partially meld the surface of the PEEK substrate and also damage the attachment of the HA coating to the PEEK surface. Such high temperature is intrinsic to the plasma spray process and cannot be avoided.

Other attempts to form an HA coating on a PEEK substrate have included mechanical attachment. However, such method resulted in a thick layer (around 100 μm) that lead to coating peel off due to mismatch of the physical properties of HA and PEEK and low fracture resistance of the HA.

The present invention overcomes these problems by applying the calcium phosphate coating at a temperature below the melting point of the polymeric material being used in the substrate. Preferably, the coating temperature is significantly below the melting point of the polymeric material. In a specific embodiment, the calcium phosphate coating is applied at ambient conditions (e.g., about room temperature or 20° C. to 20° C.). The use of the term "ambient conditions" particularly means there is no need to artificially raise or lower the temperature conditions to effect coating. However, the method would not be limited to coating at ambient temperature and would be expected to work at somewhat increased temperatures. The invention benefits, however, from the ability to carry out the coating method at ambient conditions. In particular embodiments, the calcium phosphate coating can be applied at a temperature of about 10° C. to about 200° C., about 10° C. to about 175° C., about 15° C. to about 150° C., about 15° C. to about 125° C., or about 10° C. to about 100° C.

In specific embodiments, the calcium phosphate coating is applied using Ion Beam Assisted Deposition (IBAD). Preferably, the IBAD system comprises dual ion beam sputtering using a primary beam and an assist beam. It is understood, however, that the present invention is not limited to a single type of sputtering system, but could rather be practiced with any number of similar systems readily understood by one of skill in the art. In one embodiment, the primary ion source is an 8 cm Kaufman-type ion source, used for sputtering the source material from the target, and the secondary ion source is a 3 cm Kaufman-type source, used for ion bombardment.

Use of IBAD provides multiple advantages over plasma spraying. When using IBAD, the calcium phosphate film bonds to the surface of the substrate on an atomic level, which leads to better and more consistent adhesion strength than available with plasma sprayed coating. By applying the calcium phosphate coating with an IBAD system, the calcium phosphate is deposited on the surface of the substrate molecule by molecule. This allows for the formation of intermolecular bonds, in part because of the use of the assist beam, which directs the individual molecules to the surface of the substrate. Accordingly, the inner layer of the calcium phosphate film is bonded to the surface of the substrate through intermolecular bonding with the substrate molecules. Further, such intermolecular bonding can occur between the coating molecules and the substrate molecules at or beneath the surface of the substrate. The molecule by molecule deposition of the calcium phosphate coating further allows for precise control of thickness and other physical characteristics. Accordingly, use of the IBAD system for applying the calcium phosphate coating to the substrate allows for much thinner coatings than can be applied using plasma spray techniques. Thinner coatings can provide a higher interfacial strength and better fracture resistance than thicker plasma spray coatings.

In one embodiment of the invention, the coating applied to the substrate has an overall thickness of about 100 nm to about 10 μm. In further embodiments, the coating has an overall thickness of about 200 nm to about 8 μm, about 300 nm to about 5 μm, about 500 nm to about 5 μm, about 800 nm to about 5 μm, or about 1 μm to about 5 μm. In still further embodiments, the coating has an overall thickness of about 100 nm to about 5 μm, about 200 nm to about 5 μm, about 200 nm to about 4 μm, about 500 nm to about 4 μm, or about 500 nm to about 3 μm. Coating thickness can vary depending upon the length of time of deposition, which can be controlled within close limits. Accordingly, coatings of precisely defined thicknesses can be prepared according to the method of the invention.

The method of the invention can also comprise further steps. For example, in some embodiments, it may be useful to provide the polymeric substrate with a thermal barrier coating prior to coating with the calcium phosphate. The thermal barrier coating is preferably a thin layer of any material that may be used in medical implants but that has a greater thermal resistance than the polymeric material used in the substrate to be coated. In certain embodiments, the thermal barrier layer may comprise a metal component, particularly a metal oxide. Specifically, the thermal barrier may be formed with zirconia or yttrium stabilized zirconia. The thermal barrier is particularly useful to protect the polymeric material against any thermal damage that during any additional treatment steps that may be used in the inventive method. Of course, if any high temperature treatment steps are not incorporated into the inventive method, the thermal barrier coating is optional.

The thermal barrier layer can be applied using IBAD, as described above. Moreover, it is also preferable for the thermal barrier layer to be applied at a temperature below the melting point of the polymeric material substrate. Preferably, the thermal barrier coating is applied using IBAD at ambient conditions. When it is desirable to apply a thermal barrier coating, the calcium phosphate coating can be applied directly over the thermal barrier coating, as described above.

In addition to the advantages described above in relation to improving mechanical strength and bonding with the substrate, the method of the invention is further advantageous in relation to the ability to prepare coated substrates with a functionally graded coating. Accordingly, the method of the invention provides the ability to prepare coated substrates wherein the calcium phosphate coating is in an amorphous phase distal to the substrate (i.e., near the outer or external surface of the coating) and is in a crystalline state proximal to the substrate (i.e., near the interface of the coating with the substrate). The crystallized phase is useful to achieve better mechanical and bonding strength with the substrate, and the amorphous phase is useful to achieve better osteointegration and bone formation with the matter surrounding the substrate. The coated substrate prepared according to the method of the invention has a nano-scale grain structure that closely mimics the structure of bone itself, thereby facilitating the in-growth of bone with the coated substrate, and generally improving the success of an implanted item or device.

In some embodiments, the calcium phosphate coating is predominantly in a crystalline form in an area of the coating layer proximal to the substrate, and is predominantly in an amorphous form in an area of the coating layer distal to the substrate. In some embodiments, predominantly means greater than about 50% by weight of the calcium phosphate in the coating layer is in the crystalline form. In further embodiments, at least about 60%, at least about 70%, at least about 80%, greater than about 90%, at least about 95%, at least about 96%, at least about 97%, at least about 98%, or at least about 99% by weight of the calcium phosphate is crystalline. In other embodiments, predominantly means greater than about 50% by weight of the calcium phosphate in the coating layer is amorphous. In further embodiments, at least about 60%, at least about 70%, at least about 80%, at least about 90%, at least about 95%, at least about 96%, at least about 97%, at least about 98%, or at least about 99% by weight of the calcium phosphate is amorphous.

The calcium phosphate coating may be a single layer that is functionally graded. Functionally graded can mean having a gradual change from predominantly crystalline to predominantly amorphous or predominantly amorphous to predominantly crystalline.

The IBAD method described herein applies a calcium phosphate coating that is the amorphous state. Thus, when it is desirable for the calcium phosphate coating to be in the crystalline state, the applied coating can be transformed by applying the appropriate treatment.

Accordingly, in some embodiments, it is useful according to the invention to include a treatment step for transforming the amorphous calcium phosphate coating to a crystalline calcium phosphate coating. In particular embodiments, this may comprise a heat treatment step. Typically, transforming amorphous calcium phosphate to crystalline calcium phosphate requires heating to a temperature of about 500° C. to 550° C. Since the melting point of polymeric materials is well below this temperature (e.g., PEEK melting is about 350° C. and PUs typically melt at around 200° C. or less), such heat treatment is not practical for the reasons described previously. According to the present invention, this problem has been overcome by providing alternate heat treatment methods that do not cause the polymeric substrate to be heated above its melting point.

In one embodiment, the heat treatment step is carried out in a microwave treatment. In particular, microwave radiation can be applied to the substrate with the thermal barrier coating and the calcium phosphate coating applied thereto and can be attenuated to only penetrate shallowly through the calcium phosphate coating. Thus, there is no thermal damage to the underlying polymeric substrate. Microwave is further advantageous because some polymeric materials, such as PEEK, are practically transparent to microwave radiation. Thus, the microwave treatment will only heat the calcium phosphate coating (e.g., to a crystallization temperature) and will not significantly heat the PEEK. Further, it can be beneficial to use a thermal barrier coating material (such as zirconia) that is also practically transparent to microwave radiation. Thus, the thermal barrier coating performs its function without any substantial direct heating of the thermal barrier coating itself by the microwave radiation.

Microwave heating is fast and well controlled to focus the heat at the calcium phosphate coating without damaging the polymeric substrate. Further, the technique has the advantage of preserving the integrity and strength of the polymer substrate. At the same time, the assisted beam of the IBAD system can enable the coating to form an atomically intermixed interface with the substrate that can further improve bonding strength compared to mechanical interlocking formed by plasma spraying. The application of such kinds of heat treatment enables heat treatment of the calcium phosphate coating in a very controlled and accurate manner.

In specific embodiments, the microwave heat-treatment comprises the use of a heat propagation tray. The heat propagation tray is specifically a tray (or plate) that is useful to increase the heat capacity of a thin coating on the polymeric substrate and expedite the heat treatment process before any damage can occur to the polymeric substrate. In preferred embodiments, the heat propagation tray is formed of the same material that is used as the coating. For example, a ceramic tray could be used that is formed of the same ceramic material that is used as the coating on the polymeric substrate. In a specific embodiment, when hydroxyapatite is used as the coating, the heat propagating tray may likewise be formed of hydroxyapatite.

In another embodiment, the heat treatment step is carried out in a laser treatment, preferably pulse laser. Again, the laser can be applied to the substrate with the thermal barrier coating and the calcium phosphate coating applied thereto and can be attenuated to only penetrate shallowly through the calcium phosphate coating. Thus, there is no thermal damage to the underlying polymeric substrate.

Whether heat treatment is via microwave or laser treatment, crystallization of the calcium phosphate is achieved. Moreover, the now crystallized calcium phosphate maintains its excellent bond strength resulting from the use of the IBAD system at room temperature to initially apply the coating.

Once the calcium phosphate coating has been transformed to a crystalline state, a functionally graded coating can be created. Since the IBAD method described herein results in the application of calcium phosphate in an amorphous state, in some embodiments, the method of the invention can comprise simply applying another calcium phosphate coating using the IBAD system. More particularly, this second calcium phosphate coating can again be applied at ambient conditions. Thus, the inventive method according to this embodiment results in the formation of a polymeric substrate coated with a functionally graded calcium phosphate (e.g., hydroxyapatite) coating. The calcium phosphate coating is crystalline at the interface with the substrate (i.e., proximal to the substrate) and is amorphous on the external surface (i.e., distal to the substrate).

In some embodiments, the method of the invention can further comprise manipulation of one or more of the ion beams used in the deposition process. Such manipulation could be used with any of the coating applications (e.g., the first calcium phosphate coating, the second calcium phosphate coating, any further calcium phosphate coatings, and the thermal barrier coating). In one particular embodiment of the invention, the IBAD system comprises a dual ion beam sputtering system comprising a primary beam and an assist beam, each set according to predetermined parameters. In one particular embodiment, the primary beam and the assist beam are each set at a predetermined voltage. The predetermined settings for the primary beam and the assist beam can vary depending upon the substrate to be coated, the coating material, and the exact desired properties of the coated substrate. One or more of the parameters of the primary beam and the assist beam can then be manipulated to further affect the nature of the coating on the substrate.

In one embodiment of the invention, the method can further comprise manipulating the assist beam, such as by lowering the voltage from the beginning voltage to a lower voltage. It is useful to begin the deposition process with the assist beam set at a higher voltage to facilitate better bonding strength at the interface of the coating with the substrate. After a new atomic layer has been deposited on the substrate, it is useful, according to one embodiment of the invention, to lower the voltage of the assist beam to avoid disruption of the newly formed coating layers. Preferably, the assist beam voltage is lowered after a specified period of time known to correspond to a time useful for deposition of a strongly bonded inner coating layer. In one embodiment of the invention, the assist beam voltage is lowered from the beginning voltage after a time of about 5 minutes to about 15 minutes.

The method of the invention, in addition to applying a calcium phosphate coating to a substrate, can also encompass the application of further materials. In one embodiment, the method further comprises application of one or more additional components useful for increasing the stability and mechanical properties of the calcium phosphate or for increasing the initial calcium absorption of the coating from serum. In one embodiment, the additional component includes yttrium.

The addition of the further components to the calcium phosphate coating of the invention can be by any method known in the art. When the coating is prepared according to the method of the invention, it is beneficial to include the additional component through doping of the target used in the IBAD system. The target generally comprises the material ultimately desired to be applied to the substrate. For example, in one embodiment of the invention, the target comprises an amount of hydroxyapatite. The target can further comprise an additional material particularly useful for holding the material to be sputtered. In a particular embodiment, the target comprises an amount of pressed hydroxyapatite held on a copper plate. Other types of backing material or plates can also be used, such as steel. The present invention, however, is not limited to these specific embodiments and can also comprise further materials that would be evident to one of skill in the art.

As previously noted, the additional components added to the calcium phosphate coating, while beneficial, are generally intended to be included only in a doping amount. Accordingly, it is beneficial for the method of the invention to be particularly adaptable for allowing the inclusion of a source for the one or more additional components. In one embodiment of the invention, the additional component added to the calcium phosphate coating is yttrium, and the yttrium is introduced to the coating by overlying strips of elemental yttrium on the hydroxyapatite target. For example, in one embodiment, two yttrium strips are placed in a cross pattern over the target, the strips being of a particular size such that the coating applied to the substrate exhibits the desired percentage of yttrium doping.

According to this embodiment of the invention, the percentage yttrium in the coating applied to the substrate can be determined according to the following formula:

$$Y\% = [(Y_{sa}/T_{sa}) \times (Y_{sy}/HA_{sy})] \times 100$$

wherein $Y_{sa}$ is the surface of the yttrium strips; $T_{sa}$ is the total target surface area; $Y_{sy}$ is the yttrium sputter yield; and $HA_{sy}$ is the hydroxyapatite sputter yield. Further, $Y_{sa}$ can be determined according to the following equation:

$$Y_{sa} = [(Y\% \times T_{sa} \times HA_{sy})/Y_{sy}] \times 100$$

wherein each variable is as defined above. Similarly, when other components are added to the calcium phosphate, the percentage of the component included in the final coating and surface area of the component placed on the target can be calculated according to the above equations. Therefore, the invention readily encompasses methods for including multiple different components in the coating of the invention.

In particular embodiments, an additional coating component may include antimicrobial or antibacterial components. For example, silver ions may be incorporated into the calcium phosphate coating throughout the thickness of the coating. Most known studies on the incorporation of silver ions into the coating of an implant have been through solution treatment, which could provide only a few nanometer depth of silver ions into the film. The present invention allows for antimicrobial/antibacterial components, such as silver, to be integrally included throughout the entire coating, not just at the surface in a minimal amount that is quickly dissipated.

In one embodiment, using IBAD, the sputtering target could be covered with small amounts of silver wire, which adds a small percentage of silver throughout the whole thickness of the coating, thus providing a "lifetime supply" of the antimicrobial/antibacterial component. Moreover, when the calcium phosphate coating is a functionally graded coating (i.e., amorphous at the surface and crystalline at the interface with the substrate), there will be a rapid release of the antimicrobial/antibacterial component soon after implantation of the coated substrate through rapid dissolution of the amorphous calcium phosphate coating. The dissolution rate will decrease toward the more crystalline calcium phosphate layer closer to the substrate, and the release rate of the antimicrobial/antibacterial component will likewise decrease.

In addition to the inventive method described above, the present invention is further beneficial for providing implantable medical devices that comprise a polymeric surface and are coated with a functionally graded coating. The coatings of the invention are described in terms of being functionally graded across the thickness of the coating. Functionally graded materials are understood to comprise materials wherein the composition, the microstructure, or both are locally varied so that a certain variation of the local material properties is achieved. Functionally graded coatings are particularly useful in that they can be structurally engineered to allow for discrete or continual variations in the molecular modeling of the coating. This allows for preparation of coatings with varying thermal, mechanical, and even bioactive properties across the thickness of the coating. The present invention allows for an even greater ability to engineer the coating on an atomic level to nanostructure the coating to predetermined specifications that maximize strength and durability in one phase of the coating while maximizing bioavailability (e.g., osseointegration) in another phase of the coating.

As previously described, the present invention is particularly useful for forming calcium phosphate coatings on polymeric substrates, the coatings being functionally graded such that crystallinity of the coating varies across the thickness of the coating. The phrase "degree of crystallinity," as used herein, refers to the relative percentage of the calcium phosphate material present that is in a crystalline phase versus that present in a non-crystalline phase (e.g., an amorphous phase). A high degree of crystallinity would indicate the material present is predominately in a crystalline phase. A low degree of crystallinity would indicate the material present is predominately in a non-crystalline phase.

The calcium phosphate coatings formed according to the present invention can take on different forms. In one embodiment, the calcium phosphate is present as tricalcium phosphate ($Ca_3(PO4)_2$). In another embodiment, the calcium phosphate is present as hydroxyapatite. In yet another embodiment, both tricalcium phosphate and hydroxyapatite are present. Preferably, at least a portion of the calcium phosphate is in the form of hydroxyapatite. In one particular embodiment, the calcium phosphate comprises predominantly hydroxyapatite. For purposes of simplicity, the coatings of the invention may be described throughout in relation to an embodiment of the invention wherein the calcium phosphate is hydroxyapatite. Description of the coating in terms of comprising hydroxyapatite, however, should not be interpreted as limiting the coatings to that single embodiment. Rather, the coatings can comprise other calcium phosphate materials, as previously noted.

The degree of crystallinity of the calcium phosphate in the coated substrate can vary depending upon the heat treatment step. In certain embodiments, the crystalline calcium phosphate (i.e., the heat-treated coating) is preferably predominately crystalline calcium phosphate. Of course, this can be varied based upon the extent of the heat treatment, and the invention encompasses heat-treating the coating so that at least some percentage of the calcium phosphate remains in the amorphous phase. Moreover, three, four, or even more calcium phosphate coatings could be applied, each having differing levels of heat treatment to vary the proportion of crystalline and amorphous calcium phosphate in each layer. Preferably, the outermost calcium phosphate coating is predominately amorphous to maximize osteointegration. In one embodiment, at least about 50% of the calcium phosphate in the outermost coating is amorphous calcium phosphate. Preferably, at least about 75% of the calcium phosphate in the outermost coating is amorphous calcium phosphate, more preferably at least about 90% of the calcium phosphate in the outermost coating is amorphous calcium phosphate.

Maximizing the amorphous nature of the calcium phosphate in the outermost coating increases biocompatibility, particularly by facilitating faster calcium absorption. The amorphous calcium phosphate exhibits greater biodegradability than crystalline calcium phosphate. Accordingly, the amorphous calcium phosphate coating facilitates the creation of channels and pores in the coating through which osteointegration can take place. Accordingly, the ability of surrounding bone to directly bond with the coated substrate is increased by the presence of the coating, particularly due to the presence of the outer, amorphous layer. Complete biodegradability of the coating, however, does not take place due to the presence of the crystalline calcium phosphate proximal to the substrate, which stabilizes the coating on the substrate. In this manner, the functionally graded coating facilitates integration and stabilization of the implant at the desired site of implantation. Furthermore, the coating limits competitive cell function at the implantation site.

The calcium phosphate coating applied to a polymeric substrate, as described herein, is particularly characterized by the excellent adhesion strength between the polymeric surface and the calcium phosphate coating. In particular embodiments, the adhesion strength of a calcium phosphate coating on a PEEK substrate is at least about 20 MPa, at least about 25 MPa, at least about 30 MPa, at least about 35 MPa, at least about 40 MPa, at least about 45 MPa, at least about 50 MPa, at least about 55 MPa, or at least about 60 MPa.

In addition to calcium phosphate, it is possible for the coating of the invention to include one or more additional components useful for increasing the biocompatibility, including osseointegration, of the coating. In one embodiment, the coating can comprise at least one further component commonly found in physiological bone that exhibits a high affinity between the ion of the component with calcium in serum. Examples of such further components include, but are not limited to zinc, magnesium, and fluoride. Still further, the coating can include other components not commonly found in physiological bone so long as the component exhibits a high affinity to calcium in serum. Such components are generally known to increase the stability and mechanical properties of the hydroxyapatite, as well as increasing the initial calcium absorption of the HA coating from serum. Initial calcium absorption has been shown to be critical for promoting new bone synthesis as it leads to the binding of specific proteins that selectively enhance bone cell formation in and around the coating, enhancement of bone cell attachment to the coating, and facilitation of proper function of the coating in bone integration. In one particular embodiment of the invention, the calcium phosphate coating further comprises an amount of yttrium. In another particular embodiment, the calcium phosphate coating further comprises an amount of an antimicrobial or antibacterial component, such as silver. Preferably, any further component is present only as a relatively small percentage of the calcium phosphate coating (i.e., a doping amount). In specific embodiments, the coating comprises at least 90% by weight calcium phosphate, at least 92% by weight calcium phosphate, at least 95% by weight calcium phosphate, at least 98% by weight calcium phosphate, at least 99% by weight calcium phosphate, at least 99.5% by weight calcium phosphate, or at least 99.9% by weight calcium phosphate.

The invention is particularly suited for preparing coated dental implants, coated orthopedic implants, and other types of coated prosthetics. Generally, the invention can be used in the preparation of coated substrates wherein the substrate is any of the various dental and orthopedic items previously noted. In one embodiment of the invention, there is provided a coated dental implant comprising a dentally implantable substrate having a surface comprising a polymeric material and that is at least partially coated with a calcium phosphate film that is in a crystalline form in the area of the coating layer proximal to the substrate and is in an amorphous form in the area of the coating layer distal to the substrate. In a particular embodiment, the calcium phosphate film coating the dentally implantable substrate includes calcium phosphate selected from the group consisting of hydroxyapatite, tricalcium phosphate, and mixtures thereof. In still another embodiment, the calcium phosphate film further comprises one or more additional components, such as yttrium or an antimicrobial or antibacterial component (e.g., silver).

According to another embodiment of the invention, there is provided a coated orthopedic implant comprising an orthopedically implantable substrate having a surface comprising a polymeric material that is at least partially coated with a calcium phosphate film that is in a crystalline form in an area of the coating layer proximal to the substrate and is in an amorphous form in an area of the coating layer distal to the substrate. In a particular embodiment, the calcium phosphate film coating the orthopedically implantable polymeric substrate includes calcium phosphate selected from the group consisting of hydroxyapatite, tricalcium phosphate, and mixtures thereof. In still another embodiment, the calcium phosphate film further comprises one or more additional components, such as yttrium.

EXPERIMENTAL

The present invention is more fully illustrated by the following examples, which are set forth to illustrate various embodiments of the invention and are not to be construed as limiting thereof.

Example 1

Preparation of Coated Substrate

A coated substrate was prepared by depositing a hydroxyapatite film on a polyetheretherketone substrate in a dual ion beam sputtering system. Six coated substrates were prepared.

Sample 1 was prepared by depositing a hydroxyapatite coating directly on the PEEK substrate using room temperature IBAD, while rotating the substrate. Sample 2 was prepared by depositing a hydroxyapatite coating directly on the PEEK substrate using room temperature IBAD without rotating the substrate. Sample 3 was prepared by depositing a titanium coating directly on the PEEK substrate using room temperature IBAD while rotating the substrate. Sample 4 was prepared by depositing a titanium coating directly on the PEEK substrate using room temperature IBAD without rotating the substrate. Sample 5 was prepared by depositing a titanium coating directly on the PEEK substrate using room temperature IBAD while rotating the substrate and depositing a hydroxyapatite coating over the titanium coating using room temperature IBAD while rotating the substrate. Sample 6 was prepared by depositing a titanium coating directly on the PEEK substrate using room temperature IBAD without rotating the substrate and depositing a hydroxyapatite coating over the titanium coating using room temperature IBAD without rotating the substrate.

Coating thicknesses for each coated substrate are provided below in Table 1. Bond strength for each coated substrate is provided in Table 2 (with comparative data reported for a plasma spray coated PEEK sample by S. W. Ha, et al. (1994), *Journal of Materials Science: Materials in Medicine*, 5(6-7): 481-484).

TABLE 1

| Coating | Substrate without Rotation | | Substrate with Rotation | |
|---|---|---|---|---|
| | Thickness (μm) | St. Dev. (%) | Thickness (μm) | St. Dev. (%) |
| Ti/PEEK | 1.46 | 21% | 0.79 | 51% |
| HA/PEEK | 1.93 | 58% | 0.93 | 36% |
| HA/TI/PEEK | 2.53 | 68% | 1.78 | 29% |

TABLE 2

| Coating Method | Coating | Substrate without Rotation | | Substrate with Rotation | |
|---|---|---|---|---|---|
| | | Bond Strength (Mpa) | St. Dev. (%) | Bond Strength (Mpa) | St. Dev. (%) |
| IBAD | HA/Ti/PEEK | 55.85 | 3% | 68.3 | 4% |
| | HA/PEEK | 59.72 | 10% | 72.59 | 3% |
| | Ti/PEEK | 48.67 | 12% | 55.81 | 9% |
| Plasma spray | HA/PEEK | 2.80 | 65% | — | — |

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method for preparing a biocompatible coated substrate comprising:
    a) providing a substrate having a surface comprising a polymeric material;
    b) applying a thermal barrier coating comprising a material selected from the group consisting of zirconia, yttrium stabilized zirconia, and combinations thereof to the substrate at a temperature below the melting point of the polymeric material; and
    c) applying a calcium phosphate coating to the substrate at a temperature below the melting point of the polymeric material.

2. The method of claim 1, wherein step c) comprises Ion Beam Assisted Deposition.

3. The method of claim 1, wherein step c) is carried out at ambient temperature.

4. The method of claim 1, wherein the polymeric material is polyetheretherketone (PEEK).

5. The method of claim 4, wherein the polymeric material is carbon fiber reinforced PEEK.

6. The method of claim 1, wherein the polymeric material is polyurethane.

7. The method of claim 1, wherein the thermal barrier coating is applied by Ion Beam Assisted Deposition.

8. The method of claim 1, further comprising:
    d) heat-treating the calcium phosphate coating.

9. The method of claim 8, wherein said heat-treating step comprises a microwave treatment.

10. The method of claim 8, wherein said heat-treating step comprises a laser treatment.

11. The method of claim 8, further comprising:
    e) applying a second calcium phosphate coating to the heat-treated first calcium phosphate coating at a temperature below the melting point of the polymeric material.

12. The method of claim 1, wherein the calcium phosphate coating has a thickness of about 100 nm to about 5 μm.

13. The method of claim 1, wherein the calcium phosphate coating has a thickness of about 500 nm to about 5 μm.

* * * * *

UNITED STATES PATENT AND TRADEMARK OFFICE
CERTIFICATE OF CORRECTION

PATENT NO. : 8,323,722 B2  
APPLICATION NO. : 12/505101  
DATED : December 4, 2012  
INVENTOR(S) : Afsaneh Rabiei It is certified that error appears in the above-identified patent and that said Letters Patent is hereby corrected as shown below:

In Column 1 of the Specification, after the heading "CROSS-REFERENCE TO RELATED APPLICATION" and paragraph, please add the following heading and paragraph:

FEDERALLY SPONSORED RESEARCH OR DEVELOPMENT

This invention was made with government support under grant number 0600596 awarded by the National Science Foundation. The government has certain rights to this invention.

Signed and Sealed this
Twenty-seventh Day of October, 2015

Michelle K. Lee
*Director of the United States Patent and Trademark Office*